United States Patent [19]

Foreman

[11] Patent Number: 4,459,993

[45] Date of Patent: Jul. 17, 1984

[54] CONTINUITY DETECTOR FOR HEARTBEAT RATE MEASURING SYSTEM

[75] Inventor: Richard L. Foreman, Lemon Grove, Calif.

[73] Assignee: Camino Laboratories, San Diego, Calif.

[21] Appl. No.: 410,043

[22] Filed: Aug. 20, 1982

[51] Int. Cl.³ .............................................. A61B 5/04
[52] U.S. Cl. .................................................. 128/706
[58] Field of Search .......................... 128/303.13–304, 128/908, 695, 702–712

[56] References Cited

U.S. PATENT DOCUMENTS

| | | | |
|---|---|---|---|
| 3,548,807 | 12/1970 | Crovella | 128/706 |
| 3,559,193 | 1/1971 | Savaglio et al. | 128/696 |
| 3,602,215 | 8/1971 | Parnell | 128/696 |
| 3,859,988 | 1/1975 | Lencioni, Jr. | 128/731 |
| 3,923,063 | 12/1975 | Andrews et al. | 128/303.14 |
| 4,027,663 | 6/1977 | Fischler et al. | 128/710 |
| 4,068,669 | 1/1978 | Niemi | 128/908 |
| 4,248,244 | 2/1981 | Charnitski et al. | 128/706 |
| 4,321,925 | 3/1982 | Hoborn et al. | 128/303.13 |
| 4,416,276 | 11/1983 | Newton et al. | 128/303.13 |
| 4,420,000 | 12/1983 | Bailey | 128/706 |

*Primary Examiner*—William E. Kamm
*Assistant Examiner*—Mitchell J. Shein
*Attorney, Agent, or Firm*—Fulwider, Patton, Rieber, Lee & Utecht

[57] ABSTRACT

A continuity detection method and apparatus for use in a system for monitoring a patient's EKG signal and estimating heartbeat rate. The continuity detection apparatus continuously monitors continuity between two EKG electrodes contacting the patient and inhibits the system from its measuring of heartbeat intervals whenever poor continuity is detected. This eliminates the effects on the system of any undetected heartbeats or heartbeat artifacts of the type caused by poor continuity, and thereby improves the accuracy of the system's heartbeat rate estimate.

18 Claims, 3 Drawing Figures

HEART RATE SUBROUTINE

CONTINUITY DETECTOR FOR HEARTBEAT RATE MEASURING SYSTEM

BACKGROUND OF THE INVENTION

This invention relates generally to systems for monitoring heartbeat activity and estimating heartbeat rate, and, more particularly, to systems of this kind having means for reducing or eliminating the effects of heartbeat artifacts.

One system of this particular type is described in a copending and commonly-assigned application for U.S. Pat. Ser. No. 306,329, filed in the name of Wilber H. Bailey and entitled "METHOD AND APPARATUS FOR MEASURING HEARTBEAT RATE." In the disclosed system, a pair of electrodes contact a patient at spaced locations, to produce an EKG signal indicative of heartbeat activity, and heartbeat detection means monitors the EKG signal, to detect the successive heartbeat pulses and input corresponding digital pulses to a microprocessor. The microprocessor measures the time durations between the successive pulses, converts these durations to corresponding rate measurements, and digitally filters the successive rate measurements, to produce an estimate of heartbeat rate. The digital filtering reduces the effects of heartbeat artifacts, which can be caused, for example, by poor connections between the electrodes and the patient, i.e., poor continuity, and movement of the electrode leads.

Heartbeat monitoring systems like that described above have been generally effective in estimating heartbeat rate. Even though the effects of heartbeat artifacts on these estimates, are reduced by digital filtering, the effects are nevertheless measurable and in some instances significant. Also, heartbeats that go undetected because of dropouts in continuity between the electrodes can adversely affect the heartbeat estimates. It should therefore be appreciated that there is a need for a heart rate monitoring system that further reduces the effects of heartbeat artifacts and that eliminates the effects of heartbeats that are undetected because of dropouts in continuity. The present invention fulfills this need.

SUMMARY OF THE INVENTION

The present invention is embodied in a method and apparatus for monitoring an EKG signal and estimating heartbeat rate. The apparatus includes first and second electrodes adapted to contact a patient at spaced locations and carry the EKG signal, along with heart rate means for monitoring the EKG signal and estimating heartbeat rate. In accordance with the invention, the apparatus further includes means for detecting continuity from one electrode through the patient to the other electrode and for producing a corresponding inhibit signal, along with means for inhibiting the heart rate means whenever the inhibit signal indicates a lack of continuity. Thereafter, if the inhibit signal terminates, the heart rate means is again enabled. In this way, the undesired effects of undetected heartbeats and of heartbeat artifacts caused by poor continuity are avoided.

In the preferred embodiment, the heart rate means measures the time durations of the intervals between successive heartbeats and estimates heartbeat rate based on a plurality of such time duration measurements. If the inhibit signal ever occurs, indicating a lack of continuity, the inhibit means inhibits the heart rate means from continuing to measure the time duration of the current heartbeat interval. Thereafter, if the inhibit signal terminates indicating that continuity has been restored, the inhibit means permits the heart rate means to resume measuring time durations after the occurrence of the next heartbeat.

The means for detecting continuity preferably includes means for coupling a prescribed continuity signal to the first electrode, along with detection means for detecting the difference between the amplitude of the continuity signal present at the first electrode and the amplitude of the continuity signal present at the second electrode. The detection means further compares that difference to a prescribed threshold, producing the inhibit signal whenever the threshold is exceeded. The continuity signal is preferably an ac signal having a frequency spectrum distinct from that of the EKG signal.

In another aspect of the invention, the apparatus further includes counter means for accumulating a measurement of the total amount of time the inhibit signal occurs, along with threshold detector means for inhibiting the heart rate means from monitoring the EKG signal if this measurement exceeds a prescribed threshold, e.g., 15 seconds. In the preferred embodiment, the counter means is an up/down counter that is incremented whenever the inhibit signal is present and decremented whenever the inhibit signal is not present.

Other aspects and advantages of the present invention should become apparent from the following description of the preferred embodiment, taken in conjunction with the accompanying drawings, which illustrate, by way of example, the principles of the invention.

DESCRIPTION OF THE PREFERRED EMBODIMENT

Figure 1:
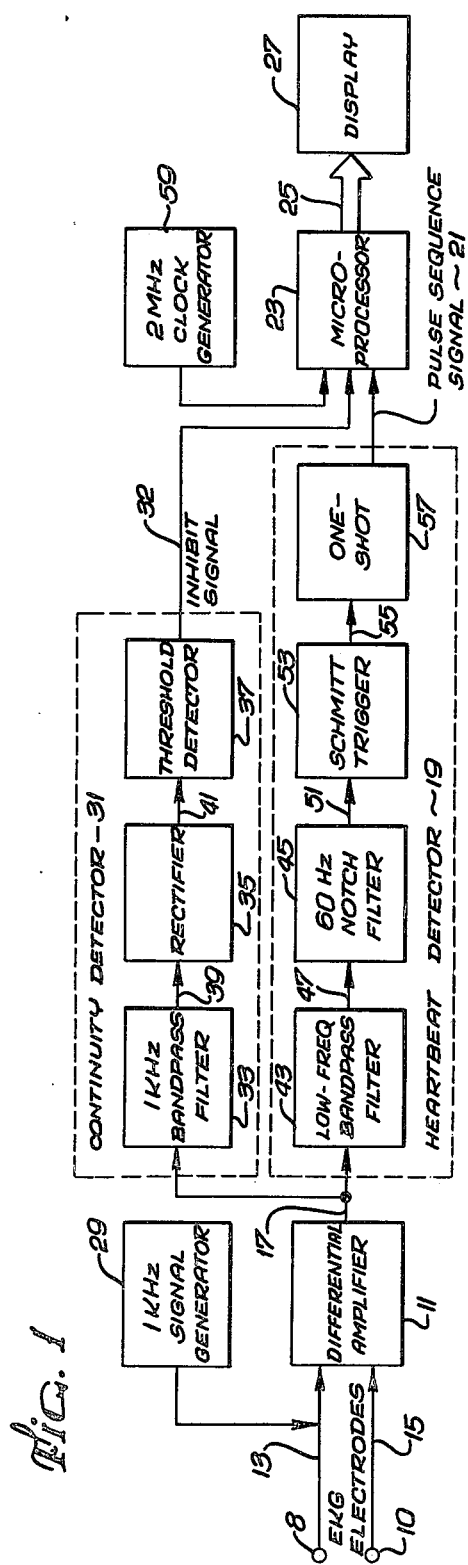
FIG. 1 is a simplified block diagram of a heart rate monitoring system having a continuity detector embodying the principles of the present invention.

Referring now to the drawings, and particularly to FIG. 1, there is shown an apparatus for monitoring a person's heartbeat activity and producing an accurate estimate of heartbeat rate. The apparatus includes first and second electrodes 8 and 10 for contacting the person in spaced relationship to each other, to develop an EKG signal indicative of heartbeat activity. A differential amplifier 11 connected to the two electrodes by a pair of leads 13 and 15, detects and amplifies the EKG signal, for coupling as a single-ended signal over line 17 to a heartbeat detector 19. The heartbeat detector filters the EKG signal to detect its successive heartbeats and output a corresponding binary pulse sequence signal for coupling on line 21 to a microprocessor 23.

The microprocessor 23 measures the time span between the successive pulses of the pulse sequence signal and converts each measurement to a corresponding rate measurement, expressed in beats per minute. After accumulating a set of 12 such rate measurements, the microprocessor digitally filters the set to reduce the effects of any heartbeat artifacts that might be included, thereby producing an estimate of average heartbeat rate.

Heartbeat artifacts can be caused by such factors as bad electrical connections between an electrode and the patient, i.e., poor continuity, coupled with movement of the electrode leads 13 and 15. The digital filtering effected by the microprocessor 23 reduces the effects of such heartbeat artifacts, but ordinarily does not completely eliminate those effects. Also, poor continuity can sometimes cause heartbeats to go undetected by the heartbeat detector 19.

In accordance with the invention, the apparatus further includes a 1 kHz signal generator 29 for coupling a 1 kHz continuity signal to the first electrode 8, along with a continuity detector 31 for determining the degree to which its amplitude is attenuated in transmission to the second electrode 10. If the continuity detector determines that the signal has been attenuated by more than a prescribed amount, it outputs an inhibit signal for coupling on line 32 to the microprocessor 23, instructing it to temporarily inhibit its measuring of the current heartbeat interval. The microprocessor resumes its measuring of heartbeat intervals if the continuity detector later determines that continuity has been restored. In this way, the effects of heartbeat artifacts and undetected heartbeats, of the type associated with a lack of continuity between the two electrodes, are eliminated and the apparatus' estimate of heartbeat rate is improved.

More particularly, the continuity detector 31 includes a 1 kHz bandpass filter 33, a rectifier 35 and a threshold detector 37. The amplified EKG signal is input to the bandpass filter on line 17 from the differential amplifier 11. Superimposed on the EKG signal is a continuity difference signal equal to the difference between the amplitudes of the respective continuity signals present at the first electrode 8 and the second electrode 10. The filter removes components of the composite EKG/continuity signal not related to the 1 kHz continuity signal. A frequency of 1 kHz is selected because it is ordinarily well above the frequency spectrum of a typical EKG signal. The filtered continuity difference signal is coupled on line 39 to the rectifier, which produces a dc level proportional to its magnitude for coupling on line 41 to the threshold detector. The threshold detector compares this dc level to a prescribed threshold, generating the inhibit signal whenever it exceeds the threshold. In the preferred embodiment, the threshold is selected such that it is exceeded whenever the impedance between the two electrodes 8 and 10 exceeds about 40K to 80K ohms.

If the two electrodes 8 and 10 are making good electrical contact with the patient, the detected continuity difference signal will have a relatively small amplitude, and after rectification, will not exceed the prescribed threshold. In that case, the inhibit signal is not produced. On the other hand, if the electrodes are not in good electrical contact with the patient, meaning that there is a poor continuity, the detected and rectified continuity difference signal will exceed the threshold, and the threshold detector will produce the inhibit signal for coupling on line 32 to the microprocessor 23.

Figure 2:
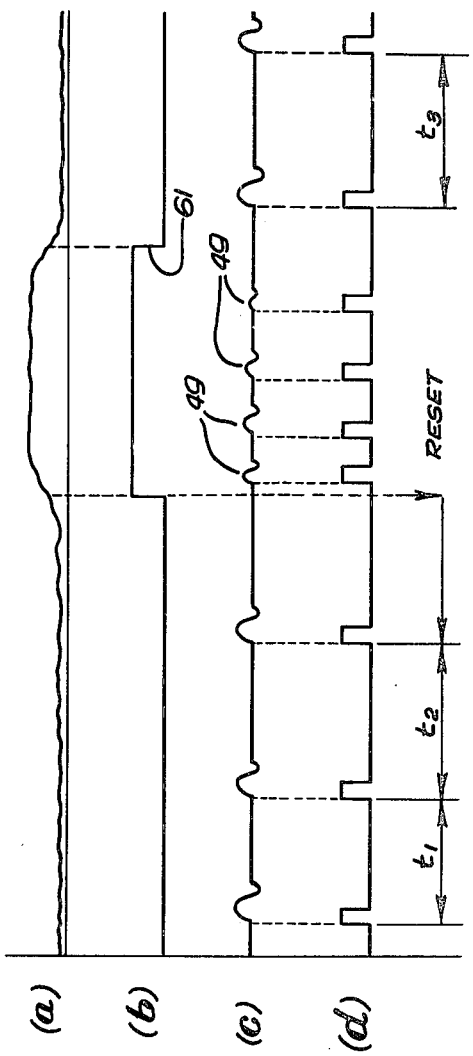
FIG. 2 is a timing diagram showing the waveforms at several different locations in the block diagram of FIG. 1.

Referring now to FIG. 2, line (a) depicts a typical rectified continuity difference signal produced by the rectifier 35 of the continuity detector 31. The relatively low levels at the left and right of the waveform are produced when good electrical contact is being made between the electrodes 8 and 10 and the patient. In the center portion of the waveform, the signal rises to a relatively high value, indicating that the continuity signal is being attenuated somewhere in the path between the two electrodes, i.e., poor continuity. Line (b) depicts the corresponding inhibit signal output by the threshold detector 37 for the rectified continuity difference signal of line (a).

Referring again to FIG. 1, the heartbeat detector 19 includes a low-frequency bandpass filter 43 and a 60 Hz notch filter 45, for removing both background noise and the continuity difference signal from the single-ended EKG signal output by the differential amplifier 11. The single-ended EKG signal is coupled over line 17 from the differential amplifier to the bandpass filter, which limits the signal to a bandwidth between about 7 and 25 Hz. This bandlimited signal is, in turn, coupled over line 47 to the 60 Hz notch filter, which removes any 60 Hz noise that might have been picked up by the electrodes 8 and 10 and electrode leads 13 and 15.

The filtered EKG signal output by the notch filter 45 (see line (c) FIG. 2) includes a number of consecutive pulses caused by actual heartbeats, and additionally might include a number of heartbeat artifacts 49 caused by some other source, in this case poor continuity between the two electrodes. The filtered EKG signal is coupled over line 51 from the notch filter to a Schmitt trigger 53, and in turn over line 55 to a monostable multi-vibrator or one-shot 57. These latter two devices convert the filtered EKG signal into the pulse sequence signal, as shown in line (d) of FIG. 2. The duration of each pulse is preferably on the order of 240 milliseconds. This pulse sequence signal is input on line 21 to the microprocessor 23.

The preferred microprocessor 23 is an RCA 1802 device, and it is associated with a random-access memory device, a read-only memory device and an address latch device (not shown). Also associated with the microprocessor are a 2 MHz clock generator 59 for appropriately sequencing it through its operations, and the display device 27 for displaying the estimate of heartbeat rate. These peripheral devices are interconnected with the microprocessor in a conventional manner, as taught in the User Manual published by RCA relating to the 1802 microprocessor. It will be understood by those of ordinary skill in the art that many other microprocessors, computers, or even hardware circuits might alternatively be used in implementing the invention.

As previously mentioned, the microprocessor 23 measures the time intervals between the successive heartbeats detected by the heartbeat detector 19. Referring to the exemplary waveform in line (d) of FIG. 2, it will be observed that the microprocessor has been able to complete its measuring of the time intervals between the first and second detected pulses and the second and third detected pulses. While measuring the interval between the third and fourth pulses, however, the inhibit signal is input to it by the continuity detector 31, indicating that continuity is no longer good between the two electrodes 8 and 10 and that the measurement of the current heartbeat interval should be terminated. The microprocessor inhibits further measuring of any pulse intervals for as long as the inhibit signal remains present. After the signal terminates, as indicated at 61 in line (b) of FIG. 2, the microprocessor waits for the next heartbeat pulse to arrive before again enabling its measurement of the next time interval.

As each interval measurement is completed, the microprocessor converts it to a corresponding rate measurement, expressed in beats per minute. After the microprocessor has accumulated a set of 12 rate measurements, it digitally filters the set to further reduce the effects of any heartbeat artifacts that might be included in the set. One suitable filtering algorithm is described in the aforementioned copending application, Ser. No. 306,329.

Figure 3:
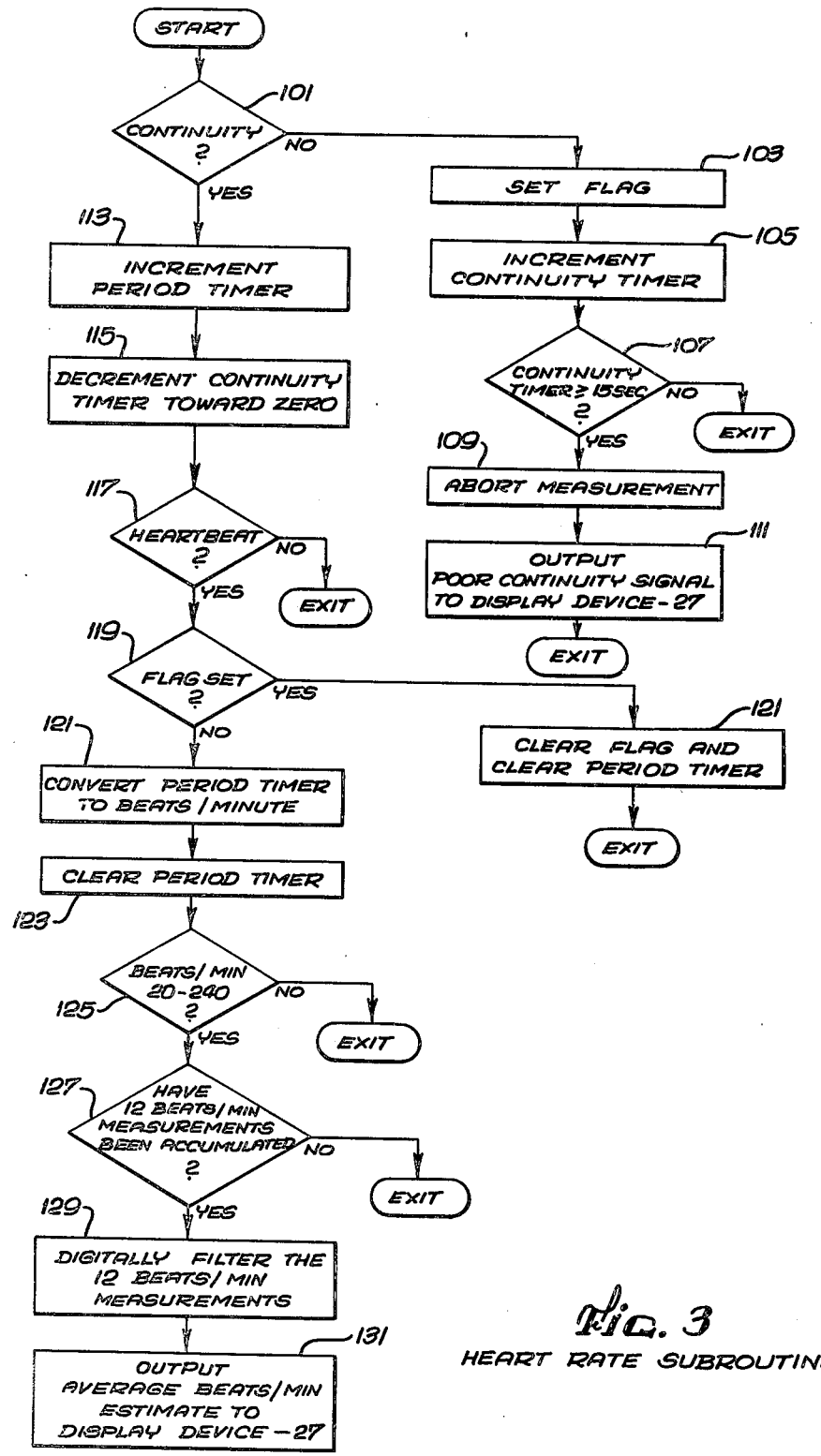
FIG. 3 is a flowchart showing, in simplified form, the operational steps performed by the microprocessor of FIG. 1.

Referring now to FIG. 3, there is shown a flowchart of a heart rate subroutine implemented by the microprocessor 23 of FIG. 1. Upon initiation of the apparatus, the microprocessor performs a first step 101 of monitoring the inhibit signal supplied on line 32, to determine whether or not poor continuity between the two electrodes has been detected. If it is determined that there is poor continuity, the microprocessor sets a "wait" flag, at step 103, and increments an internal continuity timer, at step 105. It then determines whether or not the accumulated time in the continuity timer has reached 15 seconds, at step 107. If it has, it is presumed that all of the measurements previously obtained are of questionable validity, and the microprocessor aborts its measuring of time intervals, at step 109, and outputs a poor continuity signal on lines 25 for display on the display device 27, at step 111. It then exits the heart rate subroutine. On the other hand, if it is determined at step 107 that the continuity timer has not yet reached 15 seconds, the microprocessor exits the subroutine immediately, returning to it approximately two milliseconds after it last entered it.

With reference again to step 101, if it is determined that continuity is presently good, the microprocessor 23 increments the period timer at step 113, and decrements the continuity timer towards zero at step 115. The timers are preferably incremented (or decremented) in steps of about two milliseconds, which corresponds to how often the microprocessor follows the heart rate subroutine. In step 117, the microprocessor then monitors the pulse sequence signal on line 21, to determine whether or not a heartbeat has occurred during the previous two milliseconds. If one has not occurred, the microprocessor exits the heart rate subroutine. If a heartbeat has occurred, on the other hand, the microprocessor at step 119 determines whether or not the "wait" flag is presently set. If so, it is determined that the heartbeat just detected is the first one following a period of poor continuity. The microprocessor then clears both the "wait" flag and the period timer, at step 121, and exits the subroutine. On the other hand, if it is determined at step 119 that the "wait" flag is not set, the microprocessor, at step 121, converts the time measurement currently stored in the period timer to a corresponding rate measurement, expressed in beats per minute, and, at step 123, clears the period timer, putting it in condition to measure the next heartbeat interval.

The microprocessor 23 then determines, at step 125, whether or not the rate measurement just computed is between 20 and 240 beats per minute. If it is not, it is assumed that the measurement is invalid, and the heart rate subroutine is exited. On the other hand, if it is determined that the rate measurement just computed is between 20 and 240 beats per minute, the program proceeds to step 127, where it is determined whether or not 12 rate measurements have been accumulated. If they have not, the heart rate subroutine is exited, to be returned to approximately two milliseconds after it was last entered. On the other hand, if 12 rate measurements have been accumulated, the microprocessor 23 digitally filters this set of measurements, at step 129, and outputs an estimate of heartbeat rate on lines 25 for display by the display device 27, at step 131.

It should be appreciated from the foregoing description that the present invention provides an improved apparatus and method for detecting a patient's heartbeat activity and providing a reliable estimate of heartbeat rate. The apparatus continuously monitors continuity between two electrodes contacting the patient and inhibits its measuring of heartbeat intervals whenever it detects poor continuity. This eliminates the effects of any undetected heartbeats or heartbeat artifacts caused by poor continuity, and thereby improves the accuracy of its heartbeat rate estimate.

Although the present invention has been described in detail with reference to the presently preferred embodiment, it should be understood by those of ordinary skill in the art that various modifications can be made without departing from the invention. Accordingly, the invention is limited only by the appending claims.

I claim:

1. Apparatus for monitoring a succession of heartbeats and estimating heart rate, comprising:
   first and second electrodes adapted to contact a patient and transmit an EKG signal indicative of heartbeat activity;
   heart rate means, connected to the first and second electrodes, for monitoring the EKG signal and estimating heart rate;
   means for coupling a prescribed continuity signal to the first electrode, for transmission through the patient to the second electrode;
   means for detecting the presence of the continuity signal at the second electrode and producing an inhibit signal whenever the continuity signal is not detected; and
   means for inhibiting the heart rate means in response to the inhibit signal.

2. Apparatus as defined in claim 1, wherein the detection means includes:
   means for determining the difference between the amplitude of the continuity signal present at the first electrode and the amplitude of the continuity signal present at the second electrode and for producing a corresponding amplitude signal; and
   means for comparing the amplitude signal to a prescribed threshold and for producing the inhibit signal whenever the threshold is exceeded.

3. Apparatus as defined in claim 1, wherein the continuity signal is an ac signal.

4. Apparatus as defined in claim 3, wherein the frequency spectrum of the continuity signal is distinct from that of the EKG signal.

5. Apparatus as defined in claim 1, wherein:
   the heart rate means includes
      means for measuring the time intervals between successive heartbeats, and
      means for estimating heartbeat rate based on a plurality of such time interval measurements;
   and
   the means for inhibiting inhibits the means for measuring if the inhibit signal occurs at any time between successive heartbeats.

6. Apparatus as defined in claim 1, and further including:
   counter means for accumulating a measurement of the amount of time the inhibit signal occurs; and threshold detector means for inhibiting the heart rate means from monitoring the EKG signal if the measurement exceeds a prescribed threshold.

7. Apparatus as defined in claim 6, wherein the counter means increments the measurement when the inhibit signal is present and decrements the measurement when the inhibit signal is not present.

8. Apparatus for estimating heartbeat rate, comprising:
first and second electrodes adapted to contact a patient at spaced locations and transmit an EKG signal indicative of heartbeat activity;
heart rate means connected to the first and second electrodes, for detecting the successive heartbeats of the EKG signal, and for measuring the time intervals therebetween and estimating heartbeat rate based on those measurements;
continuity detection means for detecting electrical continuity from one electrode through the patient to the other electrode, the continuity detection means including
means for coupling a prescribed continuity signal to the first electrode, for transmission through the patient to the second electrode, and
means for detecting the presence of the continuity signal at the second electrode and producing an inhibit signal whenever the continuity signal is not detected; and
inhibit means for inhibiting the heart rate means from measuring the current heartbeat interval, whenever the inhibit signal is present and at least until the heart rate means detects the first heartbeat after the inhibit signal terminates, whereby erroneous heartbeat estimates caused by a lack of continuity between the first and second electrodes are prevented.

9. Apparatus as defined in claim 8, wherein the means for detecting includes:
means for determining the difference between the amplitude of the continuity signal present at the first electrode and the amplitude of the continuity signal present at the second electrode and for producing a corresponding amplitude signal; and
means for comparing the amplitude signal to a prescribed threshold and for producing the inhibit signal whenever the threshold is exceeded.

10. Apparatus as defined in claim 8, wherein the continuity signal is an ac signal having a frequency spectrum distinct from that of the EKG signal.

11. Apparatus as defined in claim 8, and further including:
up/down counter means for accumulating a measurement of the amount of time the inhibit signal is present in excess of the amount of time the inhibit signal is not present; and
threshold detector means for inhibiting the heart rate means from estimating heartbeat rate if the up/down counter means measurement ever exceeds a prescribed threshold.

12. Apparatus for estimating heartbeat rate, comprising:
first and second electrodes adapted to contact a patient at spaced locations and transmit an EKG signal indicative of heartbeat activity;
heart rate means, connected to the first and second electrodes, for detecting the successive heartbeats of the EKG signal, measuring the time intervals therebetween, and estimating heartbeat rate based on those measurement;
continuity detection means for detecting electrical continuity from one electrode through the patient to the other electrode, the continuity detection means including
means for coupling a prescribed ac continuity signal to the first electrode, for transmission through the patient to the second electrode, the continuity signal having a frequency spectrum distinct from that of the EKG signal,
means for determining the difference between the amplitude of the continuity signal present at the first electrode and the amplitude of the continuity signal present at the second electrode and for producing a corresponding amplitude signal, and
p1 means for comparing the amplitude signal to a prescribed threshold and for producing an inhibit signal whenever the threshold is exceeded;
inhibit means for inhibiting the heart rate means from measuring the current heartbeat interval whenever the inhibit signal is present and at least until the heart rate means detects the first heartbeat after the inhibit signal terminates, whereby erroneous heartbeat estimates caused by a lack of continuity between the first and second electrodes are prevented;
up/down counter means for accumulating a measurement of the amount of time the inhibit signal is present in excess of the amount of time the inhibit signal is present in excess of the amount of time the inhibit signal is not present; and
threshold detector means for inhibiting the heart rate means from estimating heartbeat rate if the up/down counter means measurement ever exceeds a prescribed threshold.

13. A method for monitoring a succession of heartbeats and estimating heartbeat rate, comprising the steps of:
connecting first and second electrodes to a patient, for transmitting an EKG signal indicative of heartbeat activity;
monitoring the EKG signal present on the first and second electrodes, and estimating heartbeat rate;
coupling a prescribed continuity signal to the first electrode, for transmission through the patent to the second electrode;
detecting the presence of the continuity signal at the second electrode and producing an inhibit signal whenever the continuity signal is not detected; and;
inhibiting the heart rate means in response to the inhibit signal.

14. A method as defined in claim 13, wherein the step of detecting the presence of the continuity signal includes steps of:
detecting the difference between the amplitude of the continuity signal at the first electrode and the amplitude of the continuity signal at the second electrode and producing a corresponding amplitude signal; and
comparing the amplitude signal to a prescribed threshold and producing the inhibit signal whenever the threshold is exceeded.

15. A method as defined in claim 13, wherein the continuity signal is an ac signal having a frequency spectrum distinct from that of the EKG signal.

16. A method as defined in claim 13, wherein: the step of monitoring and estimating includes steps of
    measuring the time intervals between successive heartbeats, and
    estimating heartbeat rate based on a plurality of such time interval measurements; and the step of inhibiting inhibits the step of measuring if the inhibit signal occurs at any time between successive heartbeats.

17. A method as defined in claim 13, and further including steps of:
    accumulating a measurement of the amount of time the inhibit signal occurs; and
    inhibiting the step of monitoring if the measurement exceeds a prescribed threshold.

18. A method as defined in claim 17, wherein the step of accumulating increments the measurement when the inhibit signal is present and decrements the measurement when the inhibit signal is not present.

* * * * *